US 6,506,568 B2

(12) United States Patent
Shriver et al.

(10) Patent No.: US 6,506,568 B2
(45) Date of Patent: Jan. 14, 2003

(54) METHOD OF ANALYZING SINGLE NUCLEOTIDE POLYMORPHISMS USING MELTING CURVE AND RESTRICTION ENDONUCLEASE DIGESTION

(75) Inventors: Mark Shriver, Boalsburg, PA (US); Joshua M. Akey, Houston, TX (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/778,546

(22) Filed: Feb. 7, 2001

(65) Prior Publication Data

US 2002/0098484 A1 Jul. 25, 2002

Related U.S. Application Data

(60) Provisional application No. 60/181,618, filed on Feb. 10, 2000, and provisional application No. 60/196,855, filed on Apr. 12, 2000.

(51) Int. Cl.$^7$ .............................. C12Q 1/68; C12P 19/34; C07H 21/04
(52) U.S. Cl. ..................... 435/6; 435/91.1; 435/91.2; 536/23.1; 536/24.3; 536/24.33
(58) Field of Search ........................... 435/6, 91.1, 91.2; 536/23.1, 24.3, 24.33

(56) References Cited

U.S. PATENT DOCUMENTS 6,110,709 A * 8/2000 Ausubel et al. ............ 435/91.2

FOREIGN PATENT DOCUMENTS

| AU | WO 99/12031 | 3/1999 |
|----|-------------|--------|
| GB | WO 00/20633 | 4/2000 |

OTHER PUBLICATIONS

Ririe (Analytical Biochemistry (1997) vol. 245, pp. 154–160).*
Germer et al. (1999) Genome Research, vol. 9, pp. 72–78).*
Shepherd, Mervyn, et al., *Monitoring of flourenscence during DNA melting as a method for discrimination and detection of PCR products in variety indentification*, Molecular Breeding 4:, pp. 509–517 (1998).

Ririe, Kirk M., et al., *Product Differentiation by Analysis of DNA Melting Curves during the Polymerase Chain Reaction*, Analytical Biochemistry 245, pp. 154–170, (1997), Article No. AB969916.

Bohling, Sandra D., et al., *Florescence Melting Curve Analysis for the Detection of the bcl–1/JH Translocation in Mantle Cell Lymphoma*, Laboratory Investigation, vol. 79, No. 3, pp. 337–345 (1999).

W. Mathias Howell, et al., *Dynamic allele–specific hybridization*, Nature Biotechnology, vol. 17, pp. 87–88 (Jan. 1999).

Soren Germer, et al., *Single–Tub Genotyping without Oligonnucleotide Probes*, Cold Spring Harbor Laboratory Press, pp. 9:72–9:78 (1999).

Che Fang, et al., *Sequence–Dependent Separation of DNA Fragments by Capillary Electrophoresis in the Presence of SYBR® Green I*, BioTechniques, 23:58–60 (Jul. 1997).

Wittwer, Carl T., et al., *Continous Florescence Monitoring of Rapid Cycle DNA Amplification*, BioTechniques 22:130–138 (Jan. 1997).

Wittwer, C.T., et al., *The LightCycler™: A Microvolume Multisample Flourimeter with Rapid Temperature Control*, BioTechniques 22:176–18, (Jan. 1997).

* cited by examiner

Primary Examiner—Kenneth R. Horlick
Assistant Examiner—Alexander H. Spiegler
(74) Attorney, Agent, or Firm—Woodcock Washburn LLP

(57) ABSTRACT

A method for discriminating between two or more alleles which differ by only a single nucleotide is provided. This method is suitable for use in solution or on a solid phase and employs the use of restriction enzyme digestion of DNA in combination with Melting Curve Analysis. Also contemplated are specific markers to be included in melting curve analysis and melting curve genotyping experiments.

9 Claims, 7 Drawing Sheets

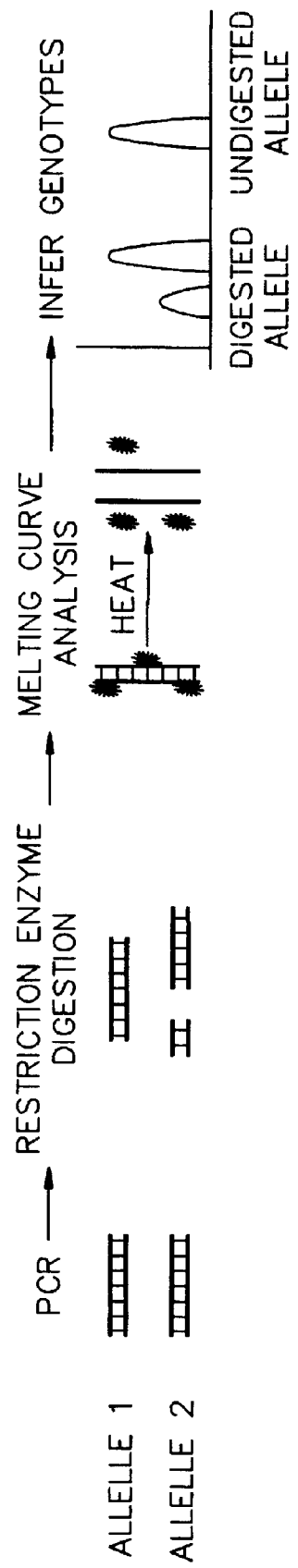

McSNP—CHIP GENOTYPING:
WHOLE PRODUCT HYBRIDIZATION PROTOCOL
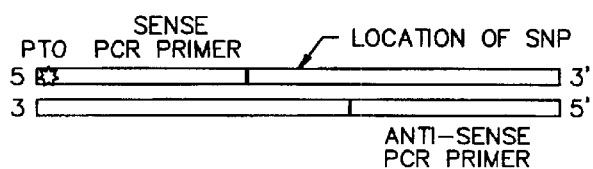
1) DIGEST PRODUCT WITH RESTRICTION ENZYME
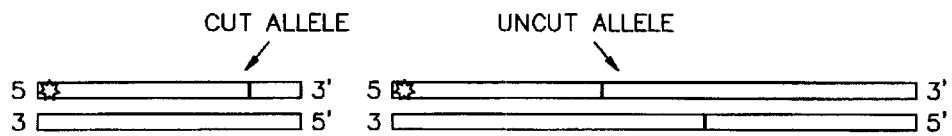
2) TREAT PCR PRODUCT WITH T7 GENE 6 EXONUCLEASE
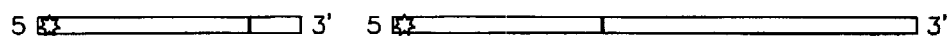
3) HYBRIDIZE TO MICROARRAY AND THEN MELT STRANDS
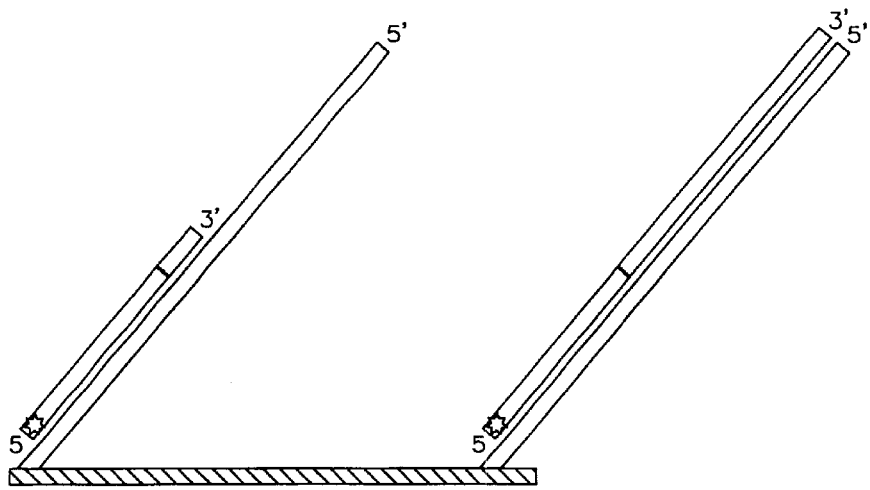
*Fig. 5*

McSNP–CHIP GENOTYPING:
PRIMER DIRECTED PROTOCOL
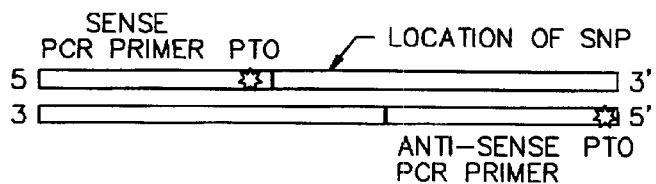
TREAT PCR PRODUCT WITH T7 GENE 6 EXONUCLEASE
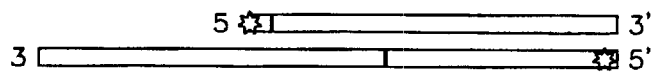
DIGEST PRODUCT WITH RESTRICTION ENZYME
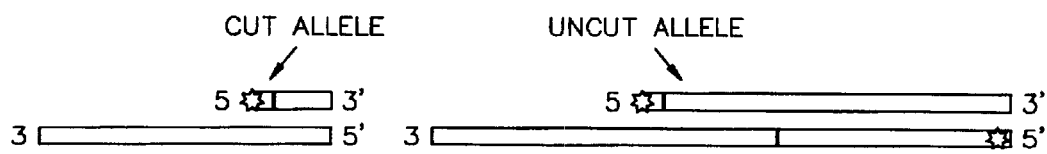
HYBRIDIZE TO MICROARRAY AND LIGATE
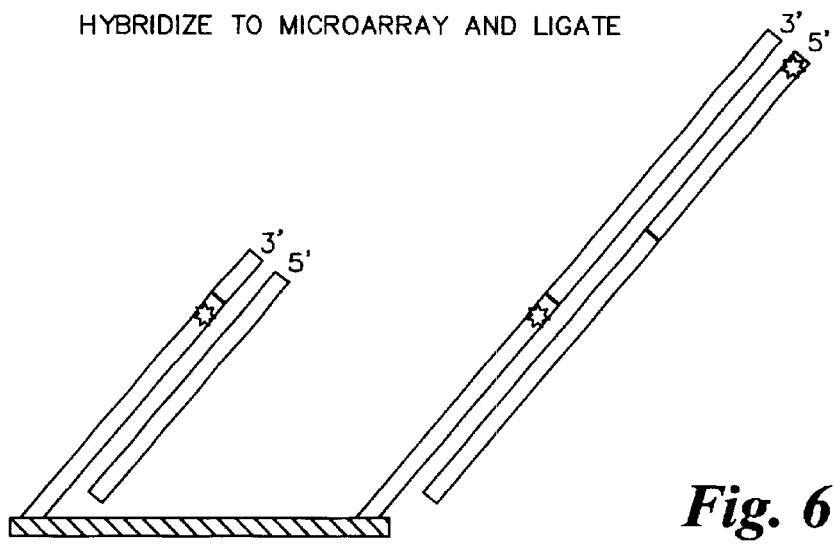
*Fig. 6* ic hybridization "DASH" (Howell, W. M., et al. (1999)

METHOD OF ANALYZING SINGLE NUCLEOTIDE POLYMORPHISMS USING MELTING CURVE AND RESTRICTION ENDONUCLEASE DIGESTION

This application claims the benefit of priority of U.S. Provisional applications Nos. 60/181,618, filed on Feb. 10, 2000, and 60/196,855, filed on Apr. 12, 2000, the contents of which are incorporated herein by reference in their entireties.

Pursuant to 35 U.S.C. 202(c), it is acknowledged that the U.S. Government has certain rights in the invention described herein, which was made in part with funds from the National Institutes of Health (DK53958 and HG02154).

FIELD OF THE INVENTION

The present invention relates to the field of molecular biology, human and non-human genetics, and metabolism and physiology. In particular, this invention provides a method for discriminating between two or more alleles that differ by only a single nucleotide. Also contemplated are specific markers to be included in melting curve analysis and melting curve genotyping experiments.

BACKGROUND OF THE INVENTION

Various publications or patents are referred to throughout this application to describe the state of the art to which the invention pertains. Each of these publications or patents is incorporated by reference herein. Complete citations of scientific publications are set forth in the text or at the end of the specification.

Single nucleotide polymorphisms (SNPs) represent the most abundant type of sequence variation in the human genome and can and should be useful tools for many diverse applications, including delineating the genetic architecture of complex traits and diseases, pharmacogenetics, forensics, and evolutionary studies.

Historically, genetic studies have been predicated on identifying and employing genetic variation to address problems of biological significance. The third generation genetic map comprised of single nucleotide polymorphisms (SNPS) is being expeditiously developed (Wang, D. G., et al. (1998) Science 280:1077–1082). SNPs are the most abundant type of sequence variation in the human genome and are useful tools in many diverse applications including disease gene mapping, evolution, pharmacogenetics, and forensics. An impressive SNP resource already exists as nearly 300,000 have been deposited into publicly accessible databases, such as the National Cancer Institute database, and others. However, without parallel progress in SNP genotyping technology, their true power and inherent benefits will not come into fruition.

Novel genotyping methods amenable to high-throughput analysis should ideally be gel-free, robust, inexpensive, and simple to perform. To this end, these requirements have inspired the development of a variety of genotyping assays, including the oligonucleotide ligation assay "OLA" (Landegren, U., et al. (1988) Science 241: 1077–80); genetic bit analysis "GBA" (Nikiforov T. T., et al. (1994) Nucleic Acids Res. 11:4167–75); mass spectroscopy (Griffin, T. J., et al. (1999) Proc Natl Acad Sci. 25: 6301–6306), "chip" technology (Wang., et al, supra), TaqMan (Livak, K. J., et al. (1995) PCR Methods Appl. 4:357–62), and dynamic allele specific hybridization "DASH" (Howell, W. M., et al. (1999) Nat. Biotechnology 17:87–88). Although many SNP genotyping methods have been developed, no single technology has emerged as being clearly superior due to limitations such as cost, complexity, and accuracy. In particular, each of these methods frequently require repeat experimentation, a high level of skill in order to perform the assays, and reagents that are costly. More importantly, currently available methods require removing samples from the reaction plate at one or more stages, such as PCR purification and the generation of single stranded DNA templates.

Kinetic PCR is predicated upon monitoring the fluorescence of a diagnostic probe once per PCR cycle (Wittwer, C. T., et al. (1997) BioTechniques 22: 130–138). Recently, the principles underlying kinetic PCR have been applied to SNP genotyping methods (Germer, S. and Higuchi, R. (1999) Genome Res 9:72–78; Howell et al., supra; Livak, et al., supra). For example, the double stranded DNA specific dye SYBR Green I (Molecular Probes, Eugene Oreg.) has been used to analyze the melting curves of PCR products. These PCR product melting curves are characterized by a rapid loss of fluorescence as the temperature is raised through the samples melting temperature ($T_m$) (Ririe, K. M., et al. (1997) Analy. Biochem. 245: 145–160). Melting temperature is a function of solution buffer, product length, sequence composition, and GC content. Thus, it should be possible to distinguish DNA fragments that differ with respect to these parameters by melting curve analysis (MCA).

Two genotyping methods have been developed that rely on MCA. The first of these entails the use of allele specific PCR whereby one of the allele specific primers contains a GC tail (Germer, et al., supra). The allele specific PCR products are then subjected to MCA and different alleles are resolved based upon which allele specific primer led to amplification. While this represents an important advance in MCA applied to SNP genotyping, it is subject to the inherent limitations of allele-specific PCR, such as difficulty in reaction optimization. This difficulty in reaction optimization decreases the overall genotyping throughput and increases the effort required to develop new SNP markers.

Another method genotypes SNPs by analyzing the melting curves of short oligonucleotide probes hybridized to a region containing the SNP of interest. Two probes are used in these reactions, each one being complimentary to a particular allele at the SNP in question. Perfectly matched probes are more stable and have a higher melting temperature compared to mismatched probes. Hence, SNP genotypes are inferred according to the characteristic melting curves produced by annealing and melting either matched or mismatched oligonucleotide probes. Similar to the first method described above, this assay has several problems including an involved experimental strategy. Specifically, PCR must be performed with biotinylated primers to allow for attachment to streptavidin coated plates. In addition, the double strand DNA must be denatured to single strand DNA with an alkali solution, followed by hybridization of the probes and finally MCA.

In order for contemporary human genetics to realize its full potential, technological advances which allow high throughput, accurate, and low-cost genotyping must be developed. Current methods for SNP genotyping have several problems such as high cost and the requirement for multiple manipulations in the laboratory. Both of these result in limitations on genotyping throughput and require highly skilled technical support. Thus, there is a particular need for gel-free single nucleotide polymorphism (SNP) genotyping methods.

SUMMARY OF THE INVENTION

The present invention provides a method for the effective gel-free analysis of single nucleotide polymorphisms. The inventive method comprises three steps: (1) DNA amplification; (2) restriction enzyme digestion; and (3) melting curve analysis. In preferred embodiments, the amplification is PCR and the DNA analyzed is less than 120 base pairs in length. Preferably, amplification, restriction enzyme digestion, and MCA are conducted in the same reaction tube(s). In preferred embodiments, the reaction and analysis time is less than 20 minutes. In highly preferred embodiments, the analysis time is less than 5 minutes.

One embodiment of the inventive method comprises the steps of amplifying at least one DNA segment of predetermined size wherein the SNP, if present, is located, the amplification further comprising introducing a selected restriction endonuclease recognition site into the segment if the segment does not contain the selected restriction endonuclease recognition site; digesting the amplification product with a restriction enzyme to produce a digested DNA product; and analyzing the melting curve of the digested DNA product by Melting Curve Analysis.

DNA amplification is conducted using standard techniques. In preferred embodiments, amplification method is PCR and comprises the steps of initial denaturation, denaturation, annealing, polymerization, and final extension. Preferably, denaturation is conducted at between 90–95° C. for 10–30 seconds. In highly preferred embodiments, denaturation is conducted at 95° C. for 30 seconds. Preferably, annealing is conducted at 45° C.–65° C. for 10–60 seconds. In highly preferred embodiments, annealing is conducted at 55° C. for 30 seconds. Preferably, extension is conducted at 72° C. for 10–90 seconds, and the final extension is conducted at 72° C. for 5 minutes. In preferred embodiments, the reaction mixture comprises genomic DNA, $MgCl_2$, 10×PCR buffer, 0.1 mM dNTPs, 0.04 uM of each primer, and 2.5 units of heat stable polymerase. In highly preferred embodiments, the heat stable polymerase is Taq polymerase. Optionally, the reaction mixture may contain SYBR Green I and Formamide or DMSO.

A critical requirement of the McSNP assay is the presence of a restriction site in the DNA generated by the SNP in one allele and not the other. In one embodiment, the restriction site is naturally occurring in one allele. In an alternative embodiment, the restriction site may be generated synthetically. The synthetic restriction site on one of the SNP alleles can be introduced by designing one of the PCR primers with a mismatch near the 3' end. In preferred embodiments, restriction enzyme reactions are comprised of PCR product, restriction enzyme, 1×reaction buffer specific for the restriction enzyme, and optionally, 1×Bovine Serum Albumin.

Preferably, melting curve analysis is performed measuring or detecting the decrease of double stranded DNA or increase of single stranded DNA. In one embodiment, double-strand DNA is detected using a dye or probe. In a preferred embodiment, the dye is a fluorescent dye. In a highly preferred embodiment, the dye is SYBR Green I. In an alternative embodiment, single-strand DNA is measured using a dye or probe. In a preferred embodiment, the dye is a fluorescent dye. In a highly preferred embodiment, the dye is SYBR Green II.

In preferred embodiments, a destabilizing agent may be added to the Melting Curve Reaction to destabilize double strand DNA and lower the Tm. In highly preferred embodiments, the destabilizing agent is DMSO and/or formamide. Optionally, automatic scoring software may be used to classify the genotypes after McSNP.

Also provided is a method for the solid phase analysis of McSNP experiments which comprises the steps of multiplexing PCR, restriction enzyme digestion, and analysis steps performed on a solid phase. In one preferred embodiment, the solid phase analysis is a Primer Directed Protocol based method. In another preferred embodiment, the solid phase analysis is Whole Product Hybridization based method.

Another aspect of the invention features specific DNA fragments to be included in melting curve analysis and melting curve SNP genotyping experiments. Methods of making melting point markers are also included in the present invention and comprise selecting a DNA sequence is that has the appropriate length and sequence for the melting point required; synthesizing the two strands of the sequence; mixing equimolar amounts of the sequences together; heating the mixture of sequences to 90° C. for approximately one minute; and allowing the mixture to cool in order to anneal the oligos together. In an alternative embodiment, the mixture of sequences are treated with a denaturating chemical gradient instead of heating. Acceptable denaturating chemicals include DMSO or formamide. Optionally, the oligos can be further labeled for fluorescence resonance energy transfer using a fluorescent dye that does not overlap in its emission spectrum with the double stranded DNA specific fluorescent dye. The annealed melting point marker is added to the restriction digested PCR product at the same time as the double strand DNA specific fluorescent dye and formamide.

BRIEF DESCRIPTION OF THE DRAWING

The invention is best understood from the following detailed description when read in connection with the accompanying drawings, in which:

FIG. 1 represents the experimental protocol of McSNP. The SNP is amplified by PCR followed by subjection to restriction enzyme digestion. The identity of each DNA fragment is determined by the unique pattern of melting curve peaks acquired by analyzing the change in fluorescence of the double stranded DNA specific dye SYBR Green I as the sample is heated. In this example, the individual is scored as a heterozygote having one undigested and one digested allele (alleles 1 and 2, respectively).

FIG. 5 depicts the Whole Product Hybridization method of McSNP-chip genotyping.

FIG. 6 depicts the Primer Directed Protocol method of McSNP-chip genotyping.

DETAILED DESCRIPTION OF THE INVENTION

Figure 2A:
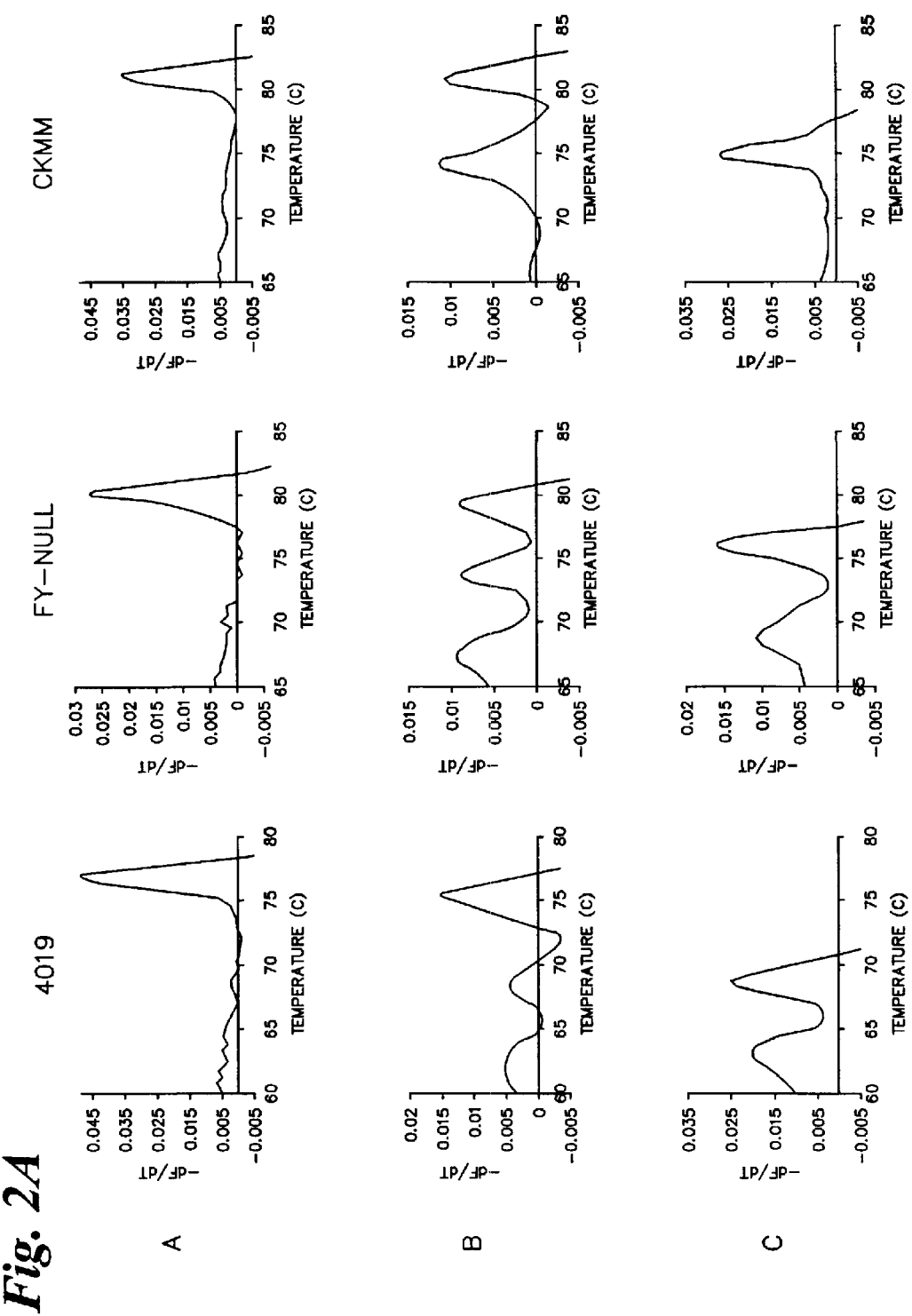
FIG. 2 shows typical McSNP profiles of six autosomal SNPs (4019, FY-null, CKMM, 14319, 14867, and LPL). Panels A, B, and C denote homozygous undigested, heterozygous, and homozygous digested genotypes, respectively. No template negative controls showed below background levels of fluorescence and are therefore not included in the figure.

The present invention is directed to a simple, inexpensive, and high-throughput assay for SNP analysis, referred to as melting curve analysis of SNPs (McSNP). The inventive method is suitable for analysis such as genotyping, forensic analysis, pharmacogenetic analysis, evolutionary studies, and delineating the genetic architecture of complex traits and diseases. McSNP combines a classic approach for discriminating alleles using restriction enzyme digestion with a more recent method for detecting DNA fragments known as melting curve analysis. The experimental data presented herein clearly demonstrates that this method is a practical, robust, and sensitive approach to assaying SNP variation. Currently available techniques such as oligonucleotide ligation assay ("OLA"), genetic bit analysis ("GBA"), chip technology and TaqMan require undue experimentation to obtain reliable results, require costly reagents, and can only be performed by one of high skill in the art. Further, these techniques require that samples be removed from the original sample tube for further analysis, such as for purification of the amplification product. In contrast to these methods, no removal of sample or portions of the sample are required in the present invention. The entire method of the present invention may be performed in a single container without removal or purification of all or a portion of the reaction.

Several currently available techniques combine PCR with Melting Curve Analysis. For example, both Ririe, et al. (Analytical Biochem. (1997) 245: 154–160) and Bohling, et al. (Laboratory Investigation (1999) 79(3): 337–345) analyzed product differentiation using analysis of DNA melting curves during PCR. However, restriction enzyme digestion was not performed in either of these methods, resulting in a discrimination only of the expected product from the primer-dimer. No discrimination was made in by either Ririe, et al. or Bohling, et al. between the mixtures of fragments within the PCR product.

Similarly, Shepherd and Henry (Molecular Breeding (1998) 4: 509–517) analyzed DNA melting curves of genotype-specific PCR fragments, but did not use restriction enzyme digestion to distinguish one DNA segment from another. Further, only one Tm was calculated for the entire PCR reaction. Thus, McSNP of the present invention is superior to currently available methods.

For any SNP analysis method, including genotyping, there are several stages that require an investment of money and time. These include designing the experiment for a specific marker, procuring reagents to type a new marker, optimizing the marker, experimentally processing the marker once it is optimized, and finally scoring the genotype results. The method of the present invention, McSNP, is superior to existing methods for all of these points. McSNP is an inexpensive, sensitive, and accurate means of SNP variation analysis. Designing or optimizing new markers is inexpensive and requires very little effort to one of skill in the art.

The inventive method comprises three steps: (1) DNA amplification; (2) restriction enzyme digestion; and (3) melting curve analysis. In preferred embodiments, the amplification is PCR and the DNA analyzed is less than 120 base pairs in length. Preferably, amplification, restriction enzyme digestion, and MCA are conducted in the same reaction tube(s). In preferred embodiments, the reaction and analysis time is less than 20 minutes. In highly preferred embodiments, the analysis time is less than 5 minutes.

In the present invention, DNA amplification is conducted using standard techniques. In preferred embodiments, amplification comprises the steps of initial denaturation, annealing, polymerization, and final extension. Amplification may be conducted in a reaction chamber. The reaction chamber may be provided with reagents for PCR including a sample polynucleotide, polymerase, nucleoside triphosphates, a first primer hybridizable with the sample polynucleotide, and a second primer hybridizable with a sequence that is complementary to the sample polynucleotide, wherein the first and second primers define the termini of the amplified polynucleotide product. The device also may include means for thermally cycling the contents of the amplification reaction chamber, such that, in each cycle, e.g., the temperature is controlled to 1) dehybridize ("melt" or "denature") double stranded polynucleotide; 2) anneal the primers to single stranded polynucleotide, and 3) synthesize amplified polynucleotide between the primers.

Preferably, denaturation is conducted at between 90–95° C. for 10–30 seconds. In highly preferred embodiments, denaturation is conducted at 95° C. for 30 seconds. Preferably, annealing is conducted at 45° C.–65° C. for 10–30 seconds. In highly preferred embodiments, annealing is conducted at 55° C. for 30 seconds. Preferably, extension is conducted at 72° C. for 10–90 seconds, and the final extension is conducted at 72° C. for 5 minutes. In preferred embodiments, the reaction mixture comprises genomic DNA, $MgCl_2$, 10×PCR buffer, 0.1 mM dNTPs, 0.04 uM of each primer, and 2.5 units of heat stable polymerase. In highly preferred embodiments, the heat stable polymerase is Taq polymerase. Optionally, the reaction mixture may contain SYBR Green I and Formamide or DMSO.

Other amplification methods available in the art may also be utilized, including, but not limited to: (1) target polynucleotide amplification methods such as self-sustained sequence replication (3SR) and strand-displacement amplification (SDA); (2) methods based on amplification of a signal attached to the target DNA, such as "branced chain" DNA amplification (Chiron Corp.); (3) methods based on amplification of probe DNA, such as ligase chain reaction (LCR) and QB replicase amplification (QBR); and (4) various other methods such as ligation activated transcription (LAT), nucleic acid sequence-based amplification (NASBA) repair chain reaction (RCR) and cycling probe reaction (CPR) (for a review of these methods, see pp.2–7 of *The Genesis Report*, DX Vol.3, No. 4, February 1994; Genesis Group, Montclair, N.J.).

After amplification, the DNA product is digested with a restriction enzyme. The presence of a restriction site generated by the SNP is a critical requirement of the McSNP assay. However, in many instances a SNP will not cause a restriction enzyme site difference. Thus, it may be necessary to introduce a convenient restriction site into the DNA. It has been estimated that SNPs occur in natural restriction sites only about 50% of the time (Landegren, et al., supra). It is estimated that 98% of all polymorphisms occur in either natural or artificial restriction sites for the commercially available 4-base cutters (Li, H. and Hood, L. (1995) Genomics 26:199–206). In these cases, a digestion site for one of the SNP alleles can be introduced by designing one of the PCR primers with a mismatch near the SNP or 3' end (Li and Hood, supra). For example, the Y-chromosome SNP M89 was genotyped with McSNP by using a primer with a mismatched C 3 bp upstream of the 3' end, thus creating a NlaIII restriction site in one of the alleles. Individuals with the M89*T allele will be undigested and produce an 87 base pair fragment, whereas those with the M89*C allele will be digested resulting in fragments of 20 and 67 base pair as seen in Table 1. Although a mismatched primer theoretically reduces the efficiency of PCR, in practice these primers are not difficult to use and do not require optimizations over that of a standard PCR reaction (Athma, P., et al. (1995) Biochem. Biophys. Res. Commun. 210: 982–986; Cohen, J. B. and Levinson, A. D. (1988) Nature 334: 119–124; Li and Hood, supra). Methods of engineering artificial restriction sites are routine, well-known to one of skill in the art, and merely require incorporation of a restriction site in the 3' end of the PCR primer. In addition to well-known laboratory techniques, computer programs are available which aid in creating artificial restriction enzyme sites.

Restriction enzymes may be considered archaic compared to some of the recent technologies developed for SNP genotyping (Griffin, et al., supra; Wang, et al., supra). However, restriction enzymes are very accurate due to their reliance upon tools that have evolved in nature to recognize SNPs. The two main disadvantages of "classic" PCR-RFLP typing are 1) limited throughput and 2) partial digestion of PCR products decreasing accuracy. These disadvantages are typically amplified by using conventional analysis methods such as agarose gel electrophoresis. However, both of these concerns are addressed by analyzing digestion products by examination of melting temperatures rather than agarose gel electrophoresis.

Throughput of gel-based methods are limited because they require substantial time and labor to pour, load, stain, and interpret gels. In contrast, McSNP reactions require very little post-amplification handling and no transfer of samples. It is possible to conduct PCR, restriction enzyme digestion, and MCA in the same multi-well plate with the analysis step requiring only minutes to perform. In preferred embodiments, the reaction and analysis time is less than 20 minutes. In highly preferred embodiments, the analysis time is less than 5 minutes.

Partial digestion is a potential problem for any method using restriction enzymes and originates primarily from either too many PCR cycles or decreased efficiency of the restriction enzyme digestion due to PCR reaction components (e.g. Triton X-100). Solutions to these problems include performing fewer PCR cycles and diluting the PCR product in a larger volume prior to restriction enzyme digestion. Both of these solutions are feasible for McSNP typing because the sensitivity of MCA is considerably higher than gel-based detection. Based on experimental results of the present invention, partial digestion does not appear to be an obstacle for the majority of McSNP experiments.

The final step of the inventive method is melting curve analysis (MCA). MCA is performed by slowly heating DNA fragments in the presence of a probe or dye that measures either the amount of decrease of double stranded DNA (dsDNA) or the increase of single stranded DNA (ssDNA) in the reaction. Suitable dyes include (but are not limited to) a dsDNA specific dye such as ethidium bromide, SYBR Green I or SYBR Green II (Molecular Probes, Eugene, Oreg.), or a ssDNA specific dye,. In preferred embodiments, the dye may be fluorescent.

As the sample is heated, fluorescence rapidly decreases when the melting temperature (Tm) of a particular fragment is reached. This rapid decrease in fluorescence is due to denaturation of the double stranded DNA. The composition of simple mixtures of DNA fragments may be determined using the present invention, including those that result from restriction enzyme digestions of short amplification products. Thus, McSNP is well suited for analysis including but not limited to high-throughput genotyping. Using currently available laboratory supplies, 96 samples can be analyzed and automatically scored in minutes in one microtiter plate. However, the present invention is well-suited for even larger sample sizes. Thus, McSNP is a simple, inexpensive, and accurate means of analysis using SNP variation.

The cost of the assay is also an important factor in analyzing SNPs. The reagent and consumable costs of a McSNP experiment are very low. The cost of a McSNP experiment is nominal beyond that of a PCR reaction, thus making it one of the lowest cost SNP analysis methods available.

A realistic estimate of sample throughput using currently available multi-well plates is 2,400 genotypes per day per instrument (96 samples/plate×25 runs/day, assuming each run requires 15 minutes). This translates into 576,000 genotypes per year (assuming 48 working weeks). Multiplexing McSNP experiments would be advantageous and time efficient. Multiplex of two loci is straightforward in principle. However, solutions containing three or more loci would likely result in complex melting curve patterns that may substantially overlap one another.

In the present invention, PCR primers are designed such that the primers flank the polymorphic site of interest. In preferred embodiments, the final PCR product size is between 50 and 150 base pairs.

Two important factors in McSNP are the size and sequence of amplification products. In particular, there is a greater difference in the $T_m$ between smaller DNA fragments than there is for larger DNA fragments. Theoretical and empirical studies of DNA denaturation have shown that as the size of DNA fragments increases, the difference in $T_m$ between them decreases. In a preferred embodiment, fragments are in the range of 50–150 base pairs in length.

Another important factor in McSNP is the use of additives that destabilize the DNA duplex and lower the $T_m$. The addition of a destabilizing agent can ensure that the $T_m$ of a fragment is reached during the experiment (i.e., $T_m<100°$ C.). Thus, in a preferred embodiment, a destabilizing agent is included. The overall effects of these additives are similar in that they destabilize dsDNA, to varying degrees, and thus lower the $T_m$. However, they have different influences on the shape of melting curves. For example, the addition of urea as a destabilizing agent resulted in broadening of peaks as well as decreasing the fluorescence of the sample and therefore made urea a less desirable additive for McSNP. TMAC is also less preferred as a destabilizing additive for the present invention, due to competition for dye binding sites. In a highly preferred embodiment, the destabilizing agent is formamide or dimethylsulfoxide (DMSO). The effects of DMSO and formamide were found to be superior compared to urea in that they resulted in more sharply defined peaks. Thus, DMSO and formamide have relatively equivalent affects on melting curve characteristics. Other suitable destabilizing agents include compounds which denature DNA by altering salt concentrations of the reaction.

Theoretical prediction of the $T_m$ of a DNA molecule is complex and has been the subject of numerous studies. In the present invention, we have empirically established a relationship between the observed and predicted $T_m$ because it is important to have some a priori information regarding the expected resolution of digested and undigested DNA fragments. The two methods used for predicting $T_m$ were: 1) a simple salt adjusted formula (Rychlik, W. and Rhoads, R. E. (1989) Nucleic Acids Res. 17:8543–8551; Sambrook, J. et al. (1989) Molecular Cloning: A Laboratory Manual, Cold Spring Harbor Laboratory Press, Cold Spring Harbor, N.Y.) and 2) a nearest neighbor algorithm (Breslauer, K. J. et al., supra).

Figure 2B:
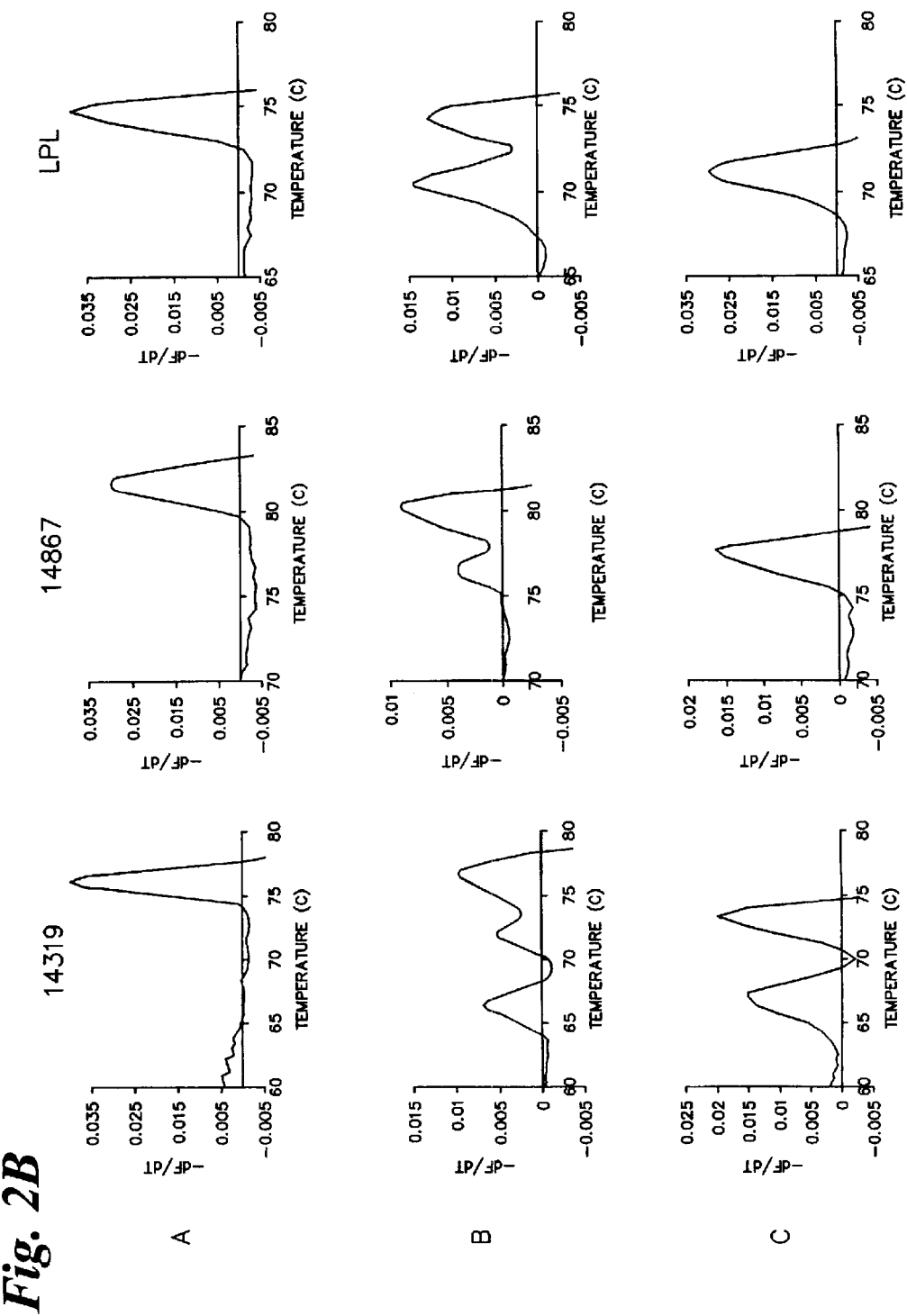
Figure 3:
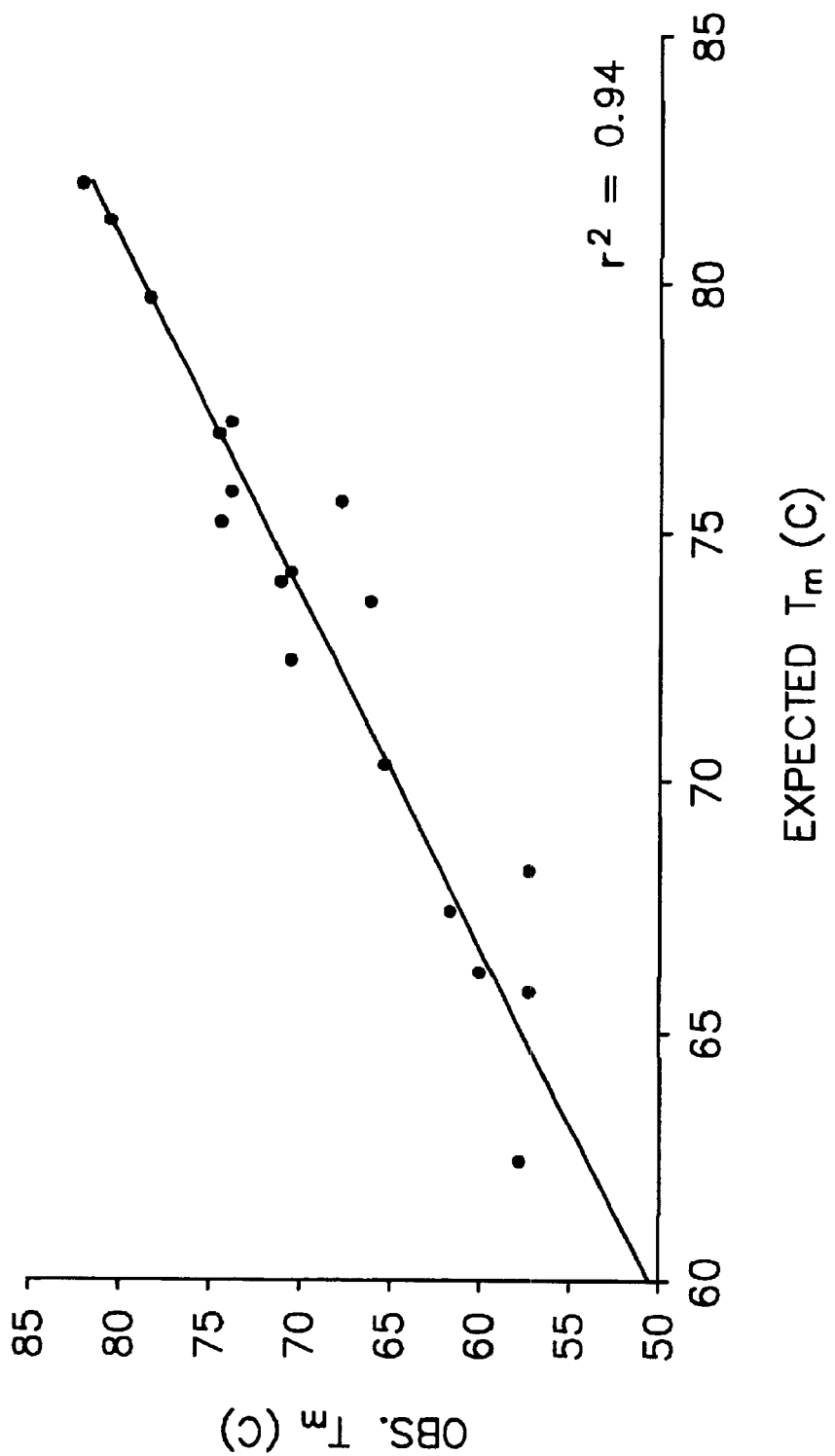
FIG. 3 shows the relationship between observed and expected $T_m$ points. A high correlation between observed and predicted $T_m$ points was observed. The predicted $T_m$ is based on a salt adjusted nearest neighbor algorithm described in Breslauer, K. J., et al. (1986) Proc Natl Acad Sci. 83: 3746–3750, and the plotted data is from Table 1.

Table 1 presents the average observed and predicted $T_m$ for all of the DNA fragments of the seven SNPs investigated based on the nearest neighbor algorithm. Similar results were obtained for the alternative formula described above. The observed $T_m$ is the average over one or two 96 well sample plates. There is a high concordance between the observed and predicted $T_m$ levels for the DNA fragments ($r^2=0.94$) shown in this table (see FIG. 3). Notable are the CKMM digest fragments (2a and 2b), which despite a 14 base pair difference in size have predicted and observed $T_m$ points that differ by only 0.2° C. and 0° C., respectively. As indicated in FIG. 2, these two fragments melt together in a single peak. Thus, the various $T_m$ prediction formulas can be used as an accurate tool in the present invention to estimate whether or not there will be a resolvable difference in $T_m$ between two DNA fragments. As an approximation, two DNA fragments can be resolved if their predicted $T_m$ difference is at least 3° C.

Furthermore, we have established the general robustness of McSNP by analysis of larger numbers of individuals and using the genotyping software of the DASH machine (WO 00/20633) to automatically score genotypes.

The experimental protocol of McSNP featuring a double strand DNA specific label is outlined in FIG. 1. FIG. 2 illustrates typical McSNP genotype profiles for six autosomal SNP loci. The peak of a melting curve denotes the $T_m$ of a particular DNA fragment, which is defined as the temperature at which half of the fragments in solution have denatured. As expected, the observed $T_m$ values of undigested SNP alleles are higher compared to the digested alleles. Notable is the clear distinction between homozygous and heterozygous individuals, where heterozygous melting curves are composites of the two homozygous melting curves.

More specifically, FIG. 2 panel A consists of homozygous undigested genotypes and thus only one $T_m$ peak is observed. Panel B contains examples of heterozygous genotypes in which one allele is digested and the other is undigested. In general, we detected two distinct types of heterozygous melting curves, in which heterozygotes formed either two (i.e., marker CKMM) or three (i.e., marker 4019, FY-null, and 14319) resolvable peaks. In three peak heterozygotes, one high temperature peak corresponds to the undigested allele, while the other two lower temperature peaks result from the two fragments produced by endonuclease cleavage of the digested allele (see FIG. 1). Conversely, in two peak heterozygotes, the two resulting DNA fragments from endonuclease cleavage of the digested allele have similar $T_m$ values and melt simultaneously. Thus, the difference between 2 and 3 peak heterozygotes is whether the digested allele gives rise to DNA fragments with the same or different $T_m$. Of note is that LPL and 14867 are actually three peak heterozygotes, but for presentation purposes the lowest $T_m$ peak was not included in the figure (see Table 1). Finally, panel C demonstrates homozygous digested genotypes. Two possible patterns of homozygous digested melting curves are possible depending on whether the digested allele results in two fragments with the same or different $T_m$.

Another embodiment of the present invention provides for a solid phase analysis of McSNP. Specifically, we have developed a modification of the McSNP protocol that allows for multiplexing the amplification, restriction enzyme digestion, and analysis steps on a solid phase or "chip." This process is referred to as McSNP-chip. The McSNP-chip method is a significant improvement over currently available chip protocols. To date, other methods that have used microarrays to analyze SNPs have relied on allele specific hybridization, which is also known as sequencing by hybridization, and on the scoring of minisequencing results. None of these efforts have included either melting curve analysis or restriction enzymes for the detection and discrimination phases of the protocols.

Collectively, McSNP solid phase improvements over currently available methods dramatically increase the throughput and significantly reduce the cost per individual SNP sample analyzed. The present invention contemplates two protocols by which this can be accomplished. In the first protocol ("Primer Directed Protocol"), a sequence specific tag is incorporated into each of the multiplexed PCR products, which are then subjected to restriction enzyme(s) digestion and hybridized to a DNA microarray chip spotted with a locus specific probe. Once this is accomplished the digestion products are fixed in place using a DNA ligase enzyme. The samples are then read by slowly increasing the temperature of the microarray support while monitoring the fluorescence. Alleles are discriminated based on their melting curve profiles, which are characterized by a rapid decrease in fluorescence as the sample passes through its melting temperature. The second protocol is different from the first ways that are outlined in the text below.

The Primer Directed Protocol method is as follows: multiplex PCR is performed by first selecting a number of SNPs which can be co-amplified and assayed by the same restriction enzyme. One of each of the pairs of PCR primers is synthesized with a phosphothioate (PTO) linkage at the immediate 3' end. The other primer in the pair has a PTO linkage as the 5' linkage in its sequence. These PTO modifications protect the strand from degradation by T7 gene 6 exonuclease. Next, these products are digested with the T7 gene 6 exonuclease in the buffer suggested by the manufacturer and then inactivated by heating to 80° C. or the addition of EDTA. Given the placement of the modifications, this step will act to produce a single-stranded locus specific probe that will be the basis of separation in subsequent steps.

After producing the single-stranded locus specific probe, the restriction enzyme is added to facilitate the discrimination of alleles. Many insertion/deletion polymorphisms can be assayed with this same protocol without the use of restriction enzymes. Several separate digestion reactions can be designed with alternate restriction enzymes included. Following the digestion, the restriction enzymes are inactivated by EDTA or heat and then combined, extracted with phenol/chloroform and precipitated with ethanol or some other process that will concentrate the digested DNA. The digestion products are then hybridized to the microarray, which has been spotted with DNA oligonucleotides that are complementary to the single stranded end of the digested DNA. A dye specific for dsDNA or ssDNA is also added at this time for detection of decrease in dsDNA or increase in ssDNA, respectively. Once the hybridization is complete, slides are washed to remove unhybridized probe and the digestion products are locked in place by the addition of DNA ligase which will covalently link the spotted locus specific oligonucleotide to the hybridized digested product.

After the oligonucleotide is covalently linked to the hybridized digested product, the melting profile of the microarray is read using a dynamic temperature microarray reader or an in situ quantitative PCR machine. The basic requirement of the reading equipment is that it can slowly heat the PTO microarray while monitoring fluorescence. In doing so, the temperature at which the bound digested products melt can be simultaneously monitored for all of the hybridized products. As an alternative to using heat to melt the samples, a gradient of chemical denaturant could be used to flow over the microarray.

The Whole Product Hybridization method comprises the following steps: Multiplex PCR is performed using one primer that has been PTO modified at the 5' end and one unmodified primer. Next, the PCR products are digested with the appropriate restriction enzymes, followed by inactivation of the enzymes. The restriction enzyme digested products are treated with T7 gene 6 exonuclease to digest all the DNA fragments that are not PTO modified at there 5' ends. These products are hybridized to microarrays with the inclusion of a dye specific for dsDNA (such as SYBR Green I, SYBR Green II, or ethidium bromide) or ssDNA to facilitate detection of dsDNA or ssDNA, respectively. For this procedure, the microarray is composed of larger tags of sequence than is required for the Primer Directed Protocol above. These sequence tags should be the complementary sequence to the strand that remains after T7 gene 6 treatment. The melting profile of the microarray is detected or read using a dynamic temperature microarray reader or an in situ quantitative PCR machine. The basic requirement of the reading equipment is that it can slowly heat the PTO microarray while monitoring fluorescence. In doing so, the temperature at which the bound digested products melt can be simultaneously monitored for all of the hybridized products. As an alternative to using heat to melt the samples, a gradient of chemical denaturant could be used to flow over the microarray. Suitable chemicals include, but are not limited to, DMSO and formamide.

Also included in the present invention is a McSNP reagent kit. This kit provides inexpensive premixed reagents for performing McSNP and other melting curve methods. In one embodiment, the kit comprises at least one melting point marker. In preferred embodiments, the melting point marker is MPM80H. MPM80H serves as a convenient positive control that can be used for temperature calibration and for trouble shooting reagents and equipment. Also included in the McSNP reagent kit are a destablizing agent and a DNA-specific fluorescent marker. In preferred embodiments, the destabilizing agent is DMSO or formamide and the fluorescent marker is SYBR Green I or SYBR Green II. In highly preferred embodiments, the destabilizing agent and fluorescent marker comprise at least 2 ml of one or more of the following combinations: 10% formamide and 2×SYBR Green I; 20% formamide and 2×SYBR Green I; 30% formamide and 2×SYBR Green I; 10% DMSO and 2×SYBR Green I; 20% DMSO and 2×SYBR Green I; or 30% DMSO and 2×SYBR Green I. Still further included in the McSNP reagent kit is a restriction enzyme in amounts suitable for multiple McSNP reactions. In prefer-red embodiments, the restriction enzyme is lyophilized. Also included in the inventive kit are primers suitable for use in McSNP reactions and TE buffer in amounts suitable for performing multiple McSNP reactions. In one highly preferred embodiment, the restriction enzyme is HindIII, the melting point marker is MPM80H, and the primers are forward primer 5' CACGAACGAT ACGCTGTCCA CCGAGCGAAG CTTTGGAAGC ACACGCACCG ACGGGGG 3'; (SEQ ID NO: 1) and reverse primer 5' CCCCCGTCGG TGCGTGTGCT TCCAAAGCTT CGCTCGGTGG ACAGCGTATC GTTCGTG 3' (SEQ ID NO:2).

Also contemplated in the present invention are Melting Point Markers (MPMs). MPMs are specific DNA fragments to be included in melting curve analysis and McSNP experiments. These fragments are small pieces of DNA (cloned, synthetic, or co-amplified with the test locus) that will also melt during the heating, phase acting as internal standards in a fashion analogous to molecular weight markers in electrophoresis. Using these MPMs one can have both internal verification of the melting run and an internal reference against which to compare the tested fragments. These two elements can be very important in particular instances where mistyping would have serious consequences, for example forensic and diagnostic applications. Additionally, in any situation where one subject is being genotyped for a number of different markers on the same plate, internal references are helpful in recognizing the patterns and can assist in automated calling of the genotypes. Differences between fragment peaks, in degrees Centigrade, remain relatively constant regardless of the concentration of formamide and other denaturants. Thus, automated scoring methods can be programmed to use the MPMs as internal references in calling (i.e., assigning) the genotypes. Further, when using instruments that can read multiple fluorophores simultaneously, the MPM can be labeled by two fluorescent dyes, such as a dsDNA specific dye, which is in the MCA or McSNP solution and a FRET (Fluorescence resonance energy transfer) dye/quencher pair at the two ends of the MPM fragment. The present invention is advantageous over that of other systems describing PCR with internal standards. For example, in Ririe, et al, supra, internal standards are limited to DNA fragments having high Tms. In contrast, the Melting Point Markers of the present invention are not limited to high Tm synthetic DNA fragments. Further, the Melting Point Markers of the present invention may be either synthetically generated or cloned DNA fragments, as opposed to the standards of Ririe, et al., which must be synthetic.

One method of making synthetic oligo melting point markers is as follows. First, a DNA sequence is selected that has the appropriate length and sequence for the melting point required. Next, the two strands of the sequence are synthesized. Equimolar amounts of the sequences are mixed together, heated to 90° C. for approximately one minute and allowed to cool in order to anneal the oligos together forming the MPM. The oligos can be labeled for FRET using second fluorescent dye that does not overlap in its emission spectrum with SYBR green I. The annealed MPM is then added to the restriction digested PCR product at the same time as the SYBR green I and formamide.

For amplification of the melting point markers using plasmids, a DNA fragment is identified which is the appropriate length and sequence. Areas where there are dramatic differences in the sequence composition should be avoided as this can lead to biphasic melting curves. Generally, using a sequence within a plasmid provides for large-scale preparations and easy separation of the fragment from other sequences.

The plasmid is then grown in host bacteria to high copy number and isolated using alkali lysis. After isolation, the plasmid is digested with the appropriate restriction enzyme (s) to create the fragment of interest. Ideally, the restriction enzyme(s) cut the plasmid so that only two fragments result; the MPM fragment and the balance of the plasmid.

Size fractionation of the digested plasmid is then accomplished by agarose gel purification, size selection filtration, gel exclusion chromatography or some other means of size selection. The fragment is then quantified and tested for purity by agarose gel electrophoresis and MCA. If it is to be used as a single labeled MPM, the fragment is in final form and needs no further processing. If a double-labeled MCS is required, quencher molecules should be added to the 3' or 5' ends of the MPS and fluorescent molecules to the complementary ends. This design will produce very little fluorescence while the MPS is double stranded and will fluoresce when denaturation occurs.

Figure 4:
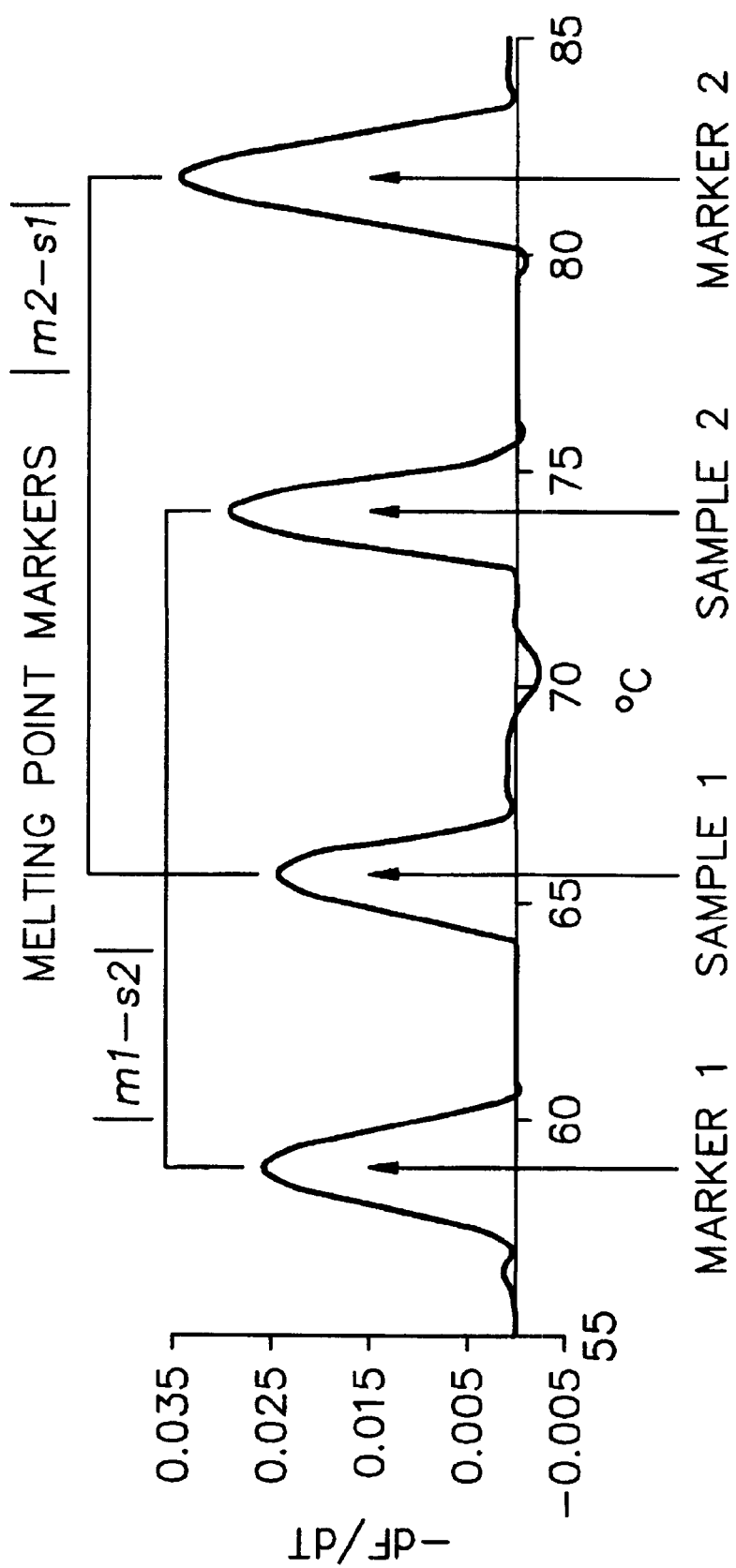
FIG. 4 is a graph of melting point markers with various samples in a MCA assay.

FIG. 4 shows how melting point markers (MPMs) can be used to help define the identity of peaks in McSNP and other genotyping methods that are based on melting curve analysis. There are four peaks resolved in this example. Two are known to be the MPMs, since they show the observed pattern in PCR-blank wells to which they have been added (Marker 1 and Marker 2). The other two peaks may or may not be present depending on the genotype of the individual being assayed. The positions of the peaks can be determined in an automated manner and the distance between the peaks then measured as the absolute value of the difference of the top of the curve in terms degrees Celsius. One could also determine the difference between the MPM peaks and use this value as a denominator in the determination of the positions, and thus the identities of the samples.

Definitions

Various terms relating to the biological molecules of the present invention are used throughout the specification and claims.

"Polymorphism" refers generally to the ability of an organism or gene to occur in two or more different forms. In particular for purposes of the present invention, "polymorphism" refers to two or more different forms of the same gene.

"Single Nucleotide Polymorphism" or "SNP" refers to a polymorphism that results from a difference in a single nucleotide.

A "restriction enzyme" or "restriction endonuclease" refers to an endonuclease which binds to double stranded DNA at a specific nucleotide sequence and then, if both strands of the DNA lack the appropriate modification at that sequence (including but not limited to methylation), cleaves the DNA either at the recognition sequence or at another site in the DNA molecule. Restriction enzymes are denoted by three letter abbreviations followed by a strain designation and/or a Roman numeral distinguishing different enzymes from the same species or strain. Recognition sequences are written 5' to 3', for one strand only. Examples of restriction enzymes include BamHI, BclI, EcoRI, HindIII, and XbaI.

The term, "allele" refers generally to any of one or more alternative forms of a given gene or DNA segment; both or all alleles of a given gene are concerned with the same trait or characteristic, but the product or function coded for by a particular allele differs, qualitatively and/or quantitatively, from that coded for by other alleles of that gene. Three or more alleles of a given gene constitute an allelomorphic series. In a diploid cell or organism the members of an allelic pair (i.e., the two alleles of a given gene) occupy corresponding positions (loci) on a pair of homologous chromosomes; if these alleles are genetically identical the cell or organism is said to be homozygous. If the alleles are genetically different, the cell or organism is said to be heterozygous with respect to the particular gene. A wild type allele is one which codes for particular phenotypic characteristic found in the wild type strain of a given organism.

The "thermal melting profile" of a DNA sample refers generally to a plot of UV absorption against temperature for a given sample of double stranded DNA. The absorption of UV radiation (at 260 nm) by two single strands of DNA is about 40% greater than that by the same strands united in a double helix. Double stranded DNA is progressively converted to single stranded DNA as the temperature increases; this conversion results in a corresponding increase in the level of UV absorption. The thermal melting profile is essentially linear between minimum absorption (all double stranded DNA) and maximum absorption (all single stranded DNA).

The "melting temperature" or "Tm" refers to the temperature at which 50% of the double strand DNA has denatured into single strand DNA. The Tm corresponds to the midpoint between the minimum UV absorption and maximum UV absorption in a thermal melting profile of a DNA sample. The Tm depends on the proportion of GC pairs in the DNA; GC pairs, having three hydrogen bonds, being more stable than AT pairs which have only two. In the presence of reagents that destabilize hydrogen bonds, the Tm is greatly reduced, and this allows strand separation to occur at much lower temperatures; under these conditions much of the damage to the DNA which may occur at high temperatures can be avoided. The Tm is affected by factors including the length of the DNA fragment, the sequence composition of the DNA fragment, salt concentration, and additive (DMSO or formamide) concentration.

The "melting curve peak" is the apex of a peak in a melting profile, thus indicating the Tm of a particular DNA fragment. Peaks result from taking the negative first derivative of fluorescence with respect to temperature.

"Multiplexing PCR" refers to the ability to amplify in tandem two or more individual SNP loci. This is a highly desirable situation since the DNA amplification step of genetic analysis is costly and time consuming. Being able to multiplex the amplification step also allows for the conservation of the genomic template DNA which is often only available in limited amounts.

The polynucleotides of the present invention may be prepared by two general methods: (1) they may be synthesized from appropriate nucleotide triphosphates, or (2) they may be isolated from biological sources. Both methods utilize protocols well known in the art. The availability of nucleotide sequence information enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

General Example

The method of McSNP comprises three steps: conducting PCR on an initial sample of DNA using a first and second PCR primer, wherein the initial sample of DNA comprises two SNP alleles; digesting the PCR product with a restriction enzyme to produce a digested DNA product; and analyzing the melting curve of the digested DNA product by Melting Curve Analysis. In preferred embodiments, the initial DNA fragments are approximately 50–150 base pairs in length. Given the small size of amplicons used in this protocol, the PCR works well under a wide variety of conditions in terms of $MgCl_2$ concentrations and annealing temperatures. Most of the PCR reactions can be conducted under a standard set of conditions. For example, in one embodiment of the present invention, reactions are performed in a total volume of 25 $\mu$l. However, the above reactions can be performed in smaller volumes to reduce cost. For example, reaction volumes as low as 5 µl are routeinly used in some laboratories. Of the total PCR product, 5 µl-the entire reaction volume is subjected to restriction enzyme digestionwith conditions as recommended by the suppliers for a period of between 30 minutes and 24 hours. Following digestion, MCA is performed. Melting profiles are analyzed in a final volume of 20 µl–100 µl. All reactions contain the digested amplified DNA1× SYBR Green I, and between 5% and 70% formamide or DMSO In one embodiment, MCA reactions are conducted in polycarbate 96 well plates (Hybaid, Oxford, UK). Real time fluorescent monitoring is performed with the DASH machine (Hybaid, Oxford, UK). Melting curves are acquired by slowly ramping the temperature from 50° C. to 90° C. at a rate of 0.04° C./sec. The total run time is approximately 15 minutes However, this total run time can be reduced once the Tm is known by adjusting the thermal range.

Fluorescence data is captured during the slow ramp to 90° C. The raw data is first converted to relative fluorescence by dividing each point by the initial fluorescence (i.e., 35° C.).

Example 1

Polymerase Chain Reaction

SNPs were amplified by PCR and most reactions were conducted under a standard set of conditions. PCR was performed in either a Hybaid Multiblock System (Hybaid, Franklin, Mass.) or GeneAmp 9700 (Applied Biosystems, Foster City, Calif.) and consisted of the following thermocycles: 95° for 5 minutes followed by 30 cycles of 95° for 30 s, 55° for 30 s, 72° for 30 s, and a final extension at 72° for 5 minutes. PCR reactions were performed in 25 µl reactions consisting of 25 ng genomic DNA, 1.5 mM $MgCl_2$, 2.5 µl 10×PCR buffer (GibcoBRL), 0.1 mM dNTPs, 0.04 µM of each primer, and 2.5 units Taq polymerase (GibcoBRL). The exception to these conditions was marker Fy-null in which the final $MgCl_2$ was 2.0 mM. Primer sequences were as follows:

| | | | |
|---|---|---|---|
| CKMM: | 5'-GCAGGCGCCTACTTCTGG-3' | (SEQ ID NO:3); | and |
| | 5'-AGCTCATGGTGGAAATGGAG-3' | (SEQ ID NO:4); | |
| 4019: | 5'-CAGGCCAAGAGCGTCcTA-3' | (SEQ ID NO:5); | and |
| | 5'-TGCCACTCTGTGAACAGCAA-3' | (SEQ ID NO:6); | |
| 14319: | 5'-CATCTGAGTGCAAGATAAAAAGGA-3' | (SEQ ID NO:7); | and |
| | 5'-CCCACCCCCAAATCATCTAT-3' | (SEQ ID NO:8); | |
| FY-null: | 5'-GCCCAGAACCTGATGGCCCTCATTAGTGCT-3' | (SEQ ID NO:9); | and |
| | 5'-CTGTCAGCGCCTGTGCTT-3' | (SEQ ID NO:10); | |
| 14867: | 5'-GGCAGGACATTCCAAGGCTCTC-3' | (SEQ ID NO:11); | and |
| | 5'-CACCCTGGGTTAACACATTCA-3' | (SEQ ID NO:12); | |
| LPL: | 5'-TGCAAGGGTTTTGCTTAATTCT-3' | (SEQ ID NO:13); | and |
| | 5'-CAACAACAAAACCCCACAGC-3' | (SEQ ID NO:14); | |
| M89: | 5'-ACAGAAGGATGCTGCTCAGCTT-3' | (SEQ ID NO:15) | and |
| | 5'-GCAACTCAGGCAAAGTGAGA<u>C</u>AT-3' | (SEQ ID NO:16), | |

Final melting curves are reported as the three point-smoothed negative first derivative of fluorescence with respect to temperature versus temperature with a base line subtraction. The baseline correction for each data point is calculated by subtracting the slope from a linear regression line encompassing four data points immediately preceding and succeeding the current point. However, software may be used which provides automated calculations. FIG. 2 displays the results of six SNPs genotyped by McSNP. Of particular note is the clear resolution of homozygous versus heterozygous genotypes for each of these six genotypes.

EXAMPLES

The following non-limiting examples are provided to describe the invention in greater detail. Unless otherwise specified, general cloning procedures, such as those set forth in Sambrook et al., Molecular Cloning, Cold Spring Harbor Laboratory (1989) (hereinafter "Sambrook et al.") or Ausubel et al. (eds) Current Protocols in Molecular Biology, John Wiley & Sons (2001) (hereinafter "Ausubel et al.") are used.

where the underlined text denotes the mismatched base to create the putative NlaIII restriction site. SNP markers WI-4019 (dbSNP ID: 2420), WI-14319, and WI-14867 were identified by querying the publicly available Whitehead Institute Genome Center SNP database. SNP markers LPL, CKMM (dbSNP ID: 5318), and FY-null were obtained from (Gotoda, T., et al. (1992) J. Lipid Res. 33:1067–1072; Gennarelli, M., et al. (1991) Hum. Genet. 87:654–656; and Tounamille, C., et al. (1995) Nat. Genet. 10:224–228, respectively. Marker M89 was obtained from Su, B., et al., (1999) Am J. Hum. Gen. 65:1718–1724. The samples used in this study represent a subset of samples comprised of African-American, European-American, and Hispanic populations. More specific details can be found elsewhere (Parra, E. J., et al. (1998) Am. J. Hum. Genet. 63:1839–1851; and Shriver, M. D., et al. (1997) Am. J. Hum. Genet. 60:957–964). Informed consent from each subject was obtained for participation in this study.

Example 2
Restriction Enzyme Digestion

Restriction enzyme digestions were performed in a final volume of 25 µl which consisted of the following: 10 µl of PCR product, 1 unit of the appropriate restriction enzyme, 1×reaction buffer supplied with the restriction enzyme, and when recommended by the supplier 1×BSA. In particular, markers 4019, M89, and 14867 were digested by the restriction enzyme NlaIII, while markers CKMM, 14319, FY-null, and LPL were digested by the restriction enzymes TaqI, RsaI, StyI, and PvuII, respectively. It was not necessary to purify the PCR products before restriction enzyme digestions, which were performed as recommended by the suppliers for a period of between 4 and 24 hours. All restriction enzymes were purchased from New England Biolabs (Beverly, Mass.).

Example 3

Melting Curve Analysis (MCA)

Melting profile reactions were analyzed in a final volume of 50 μl. All reactions contained 5 μl of restriction enzyme digested DNA reaction mixture, 5 μl 10×SYBR Green I (which comes as a 10,000×stock supplied by the manufacturer, Molecular Probes, Eugene, Oreg.), and were brought to a final volume of 50 μl in ddH$_2$O. Various destabilizing agents were added to these reactions including formamide (Fisher Biotech, Fair Lawn, N.J.), DMSO (Fisher Biotech, Fair Lawn, N.J.), and urea (Fisher Biotech, Fair Lawn, N.J.). Here we provide the details of only those additives that had an enhancing affect on melting curse analysis. The optimal final concentrations of these additives were 5–70% formamide or 5–70% DMSO. All reactions were performed in polycarbonate multi-well plates (Hybaid, Franklin, Mass.). Real time fluorescent monitoring was performed with the DASH machine (Hybaid, Franklin, Mass.). Other currently available instruments that may be suitable for MCA include the PE-5700 and PE-7700 (Applied Biosystems, Foster City, Calif.), Light Cycler (Roche, Idaho Falls, Id.), iCycler (BioRad, Hercules, Calif.), Smart Cycler (Cephied, Sunnyvale, Calif.), and Sentinel (Stratagene, La Jolla, Calif.).

Melting curves are acquired by ramping the temperature from 35° C. to 90° C. at a rate of 0.04° C./sec, and monitoring the change in fluorescence of SYBR Green I at 520 nm. The total run time is approximately 22 minutes, which can be generally cut in half once the $T_m$ is known by adjusting the thermal range. It is during the slow ramp to 90° C. when the fluorescence is captured. The raw data is first converted to relative fluorescence by dividing each point by the initial fluorescence (i.e., 35° C.) (Germer, et al., supra). Final melting curves are reported as three point-smoothed negative first derivative of fluorescence with respect to temperature versus temperature with a base line subtraction. The baseline correction for each data point is calculated by subtracting the slope from a linear regression line of the first nine data points. All genotypes were confirmed by agarose-gel electrophoresis. Specifically, samples were amplified by a second set of PCR primers to produce larger products more suitable for scoring by agarose-gel electrophoresis. These samples were then independently digested and scored by agarose gels.

Example 4

Automated Scoring

In order to investigate the utility and robustness of McSNP on a larger scale we genotyped 853 individuals for marker CKMM. Moreover, we used the automatic scoring feature of the DASH software (v. 2.14), which allows genotypes to be 'called' (i.e., assigning genotypes to individual samples) automatically after an experiment is complete. Of the 853 samples, 37 failed to amplify (i.e., PCR failures). Of the remaining 816 samples, 807 were correctly genotyped and scored (98.9%). Thus, only 1.1% (9 individuals) of the reactions that were amplified and automatically scored with the DASH software were repeated due to inconsistencies with the observed melting curve pattern. These problems can be classified into two categories: 1) Unusual patterns in the relative size of the melting curves (0.7%). These patterns are likely due to partial digestion of the PCR products, and after subsequent amplification and digestion with increased amounts of enzyme and/or fewer PCR cycles, the samples show the expected melting profiles. 2) Unusual peaks in the scoring range (0.4%), which disappeared when the same samples were amplified, digested, and scored again with the DASH software. These problems are attributable to artifacts in the amplification or monitoring of the $T_m$ profile. Overall, the automatic scoring feature of the DASH software allows a fast and accurate classification of genotypes. However, a careful inspection of the automatic scores is recommended in order to detect and correct possible errors due to PCR artifacts or partial digestion.

The present invention is not limited to the embodiments described and exemplified above, but is capable of variation and modification within the scope of the appended claims.

TABLE 1

A comparison of observed and predicted $T_m$'s

| Locus | Fragment sizes (bp)[a] | Observed $T_m$ (° C.) | Predicted $T_m$ (° C.)[b] | Observed \|1–2a\| (° C.)[c] | Predicted \|1–2a\| (° C.) | Observed \|1–2b\| (° C.)[d] | Predicted \|1–2b\| (° C.) | Observed \|2a–2b\| (° C.)[e] | Predicted \|2a–2b\| (° C.) |
|---|---|---|---|---|---|---|---|---|---|
| CKMM | 1:82 | 1:82.0 | 1:84.3 | | | | | | |
| | 2a:48 | 2a:74.1 | 2a:73.5 | 7.9 | 10.7 | 7.9 | 10 | 0 | 0.2 |
| | 2b:34 | 2b:74.1 | 2b:73.7 | | | | | | |
| 4019 | 1:62 | 1:77.4 | 1:72.2 | | | | | | |
| | 2a:25 | 2a:67.4 | 2a:63.8 | 10 | 13.3 | 15 | 15 | 5 | 4.1 |
| | 2b:37 | 2b:62.4 | 2b:59.7 | | | | | | |
| FY-null | 1:61 | 1:80 | 1:78.4 | | | | | | |
| | 2a:38 | 2a:75.5 | 2a:68.1 | 6 | 10.1 | 10 | 14 | 7.9 | 11.1 |
| | 2b:23 | 2b:68.2 | 2b:57.2 | | | | | | |
| 14319 | 1:84 | 1:76.1 | 1:76.5 | | | | | | |
| | 2a:52 | 2a:73.4 | 2a:68.1 | 4.7 | 8.4 | 11.8 | 21 | 5.3 | 6.1 |
| | 2b:32 | 2b:66.1 | 2b:73.6 | | | | | | |

TABLE 1-continued

A comparison of observed and predicted $T_m$'s

| Locus | Fragment sizes (bp)[a] | Observed $T_m$ (° C.) | Predicted $T_m$ (° C.)[b] | Observed \|1–2a\| (° C.)[c] | Predicted \|1–2a\| (° C.) | Observed \|1–2b\| (° C.)[d] | Predicted \|1–2b\| (° C.) | Observed \|2a–2b\| (° C.)[e] | Predicted \|2a–2b\| (° C.) |
|---|---|---|---|---|---|---|---|---|---|
| 14867 | 1:81 | 1:81.4 | 1:80.4 | | | | | | |
| | 2a:52 | 2a:77.7 | 2a:74.6 | 3.7 | 5.8 | 15.7 | 19 | 12 | 5.8 |
| | 2b:29 | 2b:65.7 | 2b:57.1 | | | | | | |
| LPL | 1:70 | 1:74.4 | 1:71.0 | | | | | | |
| | 2a:51 | 2a:70.4 | 2a:65.5 | 4 | 5.5 | 18.3 | 28 | 14.3 | 22 |
| | 2b:19 | 2b:56.1 | 2b:43.5 | | | | | | |
| M89 | 1:87 | 1:75.5 | 1:75.3 | | | | | | |
| | 2a:57 | 2a:72.1 | 2a:70.9 | 3.4 | 4.4 | 29.4 | 29.9 | 26 | 25.5 |
| | 2b:20 | 2b:45.4 | 2b:46.1 | | | | | | |

[a]Fragment size refers to the size of DNA fragments that result from restriction enzyme digestion. Fragments labeled 1 denote the fragment that results for undigested alleles, while fragments 2a and 2b are those that result for digested alleles
[b]predicted $T_m$ is based on a salt adjusted nearest neighbor algorithm described in the text (2)
[c,d,e]denotes the absolute value of the difference in observed $T_m$s for fragments 1 and 2a, 1 and 2b, and 2a and 2b, respectively

What is claimed is:

1. A method for gel-free analysis of single nucleotide polymorphisms (SNPs) comprising the steps of amplifying at least one DNA segment suspected of containing a SNP to produce an amplified DNA segment, wherein the amplifying is performed using a first primer and a second primer;

digesting the amplified DNA segment with a selected restriction endonuclease to produce a digested amplified DNA segment, wherein digestion of the DNA segment with a selected restriction endonuclease produces a cleaved DNA if the SNP is present in the DNA segment;

generating a melting curve of the digested amplified DNA segment by melting curve analysis; and determining from the melting curve the presence or absence of the SNP.

2. The method of claim 1 wherein the steps are conducted in a single tube.

3. The method of claim 1 comprising the additional step of generating within the DNA segment a cleavage site for the selected restriction endonuclease; the step comprising modifying the first or second primer, or both, at or near the 3' end.

4. The method of claim 1 wherein the melting curve analysis measures a change in double stranded DNA.

5. The method of claim 1 wherein the melting curve analysis measures a change in single stranded DNA.

6. The method of claim 1 wherein the melting curve analysis is conducted in the presence of a destablizing agent.

7. The method of claim 6 wherein the destabilizing agent is DMSO or formamide.

8. The method of claim 1 wherein the melting curve analysis is conducted in the presence of at least one melting point marker.

9. The method of claim 1 wherein the analysis of the SNP is conducted on a solid phase.

* * * * *

SEQUENCE LISTING

<160> NUMBER OF SEQ ID NOS: 16

<210> SEQ ID NO 1
<211> LENGTH: 57
<212> TYPE: DNA
<213> ORGANISM: Artificial Sequence
<220> FEATURE:
<223> OTHER INFORMATION: synthetic sequence

<400> SEQUENCE: 1
cacgaacgat acgctgtcca ccgagcgaag ctttggaagc acacgcaccg acggggg    57

<210> SEQ ID NO 2
<211> LENGTH: 57
<212> TYPE: DNA
<213> ORGANISM: Artificial Sequence
<220> FEATURE:
<223> OTHER INFORMATION: synthetic sequence

<400> SEQUENCE: 2
cccccgtcgg tgcgtgtgct tccaaagctt cgctcggtgg acagcgtatc gttcgtg    57

<210> SEQ ID NO 3
<211> LENGTH: 18
<212> TYPE: DNA
<213> ORGANISM: Artificial Sequence
<220> FEATURE:
<223> OTHER INFORMATION: synthetic sequence

<400> SEQUENCE: 3
gcaggcgcct acttctgg                                                18

<210> SEQ ID NO 4
<211> LENGTH: 20
<212> TYPE: DNA
<213> ORGANISM: Artificial Sequence
<220> FEATURE:
<223> OTHER INFORMATION: synthetic sequence

<400> SEQUENCE: 4
agctcatggt ggaaatggag                                              20

```
<210> SEQ ID NO 5
<211> LENGTH: 18
<212> TYPE: DNA
<213> ORGANISM: Artificial Sequence
<220> FEATURE:
<223> OTHER INFORMATION: synthetic sequence

<400> SEQUENCE: 5
caggccaaga gcgtccta                                                    18

<210> SEQ ID NO 6
<211> LENGTH: 20
<212> TYPE: DNA
<213> ORGANISM: Artificial Sequence
<220> FEATURE:
<223> OTHER INFORMATION: synthetic sequence

<400> SEQUENCE: 6
tgccactctg tgaacagcaa                                                  20

<210> SEQ ID NO 7
<211> LENGTH: 24
<212> TYPE: DNA
<213> ORGANISM: Artificial Sequence
<220> FEATURE:
<223> OTHER INFORMATION: synthetic sequence

<400> SEQUENCE: 7
catctgagtg caagataaaa agga                                             24

<210> SEQ ID NO 8
<211> LENGTH: 20
<212> TYPE: DNA
<213> ORGANISM: Artificial Sequence
<220> FEATURE:
<223> OTHER INFORMATION: synthetic sequence

<400> SEQUENCE: 8
cccaccccca aatcatctat                                                  20

<210> SEQ ID NO 9
<211> LENGTH: 30
<212> TYPE: DNA
<213> ORGANISM: Artificial Sequence
<220> FEATURE:
<223> OTHER INFORMATION: synthetic sequence

<400> SEQUENCE: 9
gcccagaacc tgatggccct cattagtgct                                       30

<210> SEQ ID NO 10
<211> LENGTH: 18
<212> TYPE: DNA
<213> ORGANISM: Artificial Sequence
<220> FEATURE:
<223> OTHER INFORMATION: synthetic sequence

<400> SEQUENCE: 10
ctgtcagcgc ctgtgctt                                                    18

<210> SEQ ID NO 11
<211> LENGTH: 22
<212> TYPE: DNA
<213> ORGANISM: Artificial Sequence
<220> FEATURE:
<223> OTHER INFORMATION: synthetic sequence
```

-continued

<400> SEQUENCE: 11
ggcaggacat tccaaggctc tc                                          22

<210> SEQ ID NO 12
<211> LENGTH: 21
<212> TYPE: DNA
<213> ORGANISM: Artificial Sequence
<220> FEATURE:
<223> OTHER INFORMATION: synthetic sequence

<400> SEQUENCE: 12
caccctgggt taacacattc a                                           21

<210> SEQ ID NO 13
<211> LENGTH: 22
<212> TYPE: DNA
<213> ORGANISM: Artificial Sequence
<220> FEATURE:
<223> OTHER INFORMATION: synthetic sequence

<400> SEQUENCE: 13
tgcaagggtt ttgcttaatt ct                                          22

<210> SEQ ID NO 14
<211> LENGTH: 20
<212> TYPE: DNA
<213> ORGANISM: Artificial Sequence
<220> FEATURE:
<223> OTHER INFORMATION: synthetic sequence

<400> SEQUENCE: 14
caacaacaaa accccacagc                                             20

<210> SEQ ID NO 15
<211> LENGTH: 22
<212> TYPE: DNA
<213> ORGANISM: Artificial Sequence
<220> FEATURE:
<223> OTHER INFORMATION: synthetic sequence

<400> SEQUENCE: 15
acagaaggat gctgctcagc tt                                          22

<210> SEQ ID NO 16
<211> LENGTH: 23
<212> TYPE: DNA
<213> ORGANISM: Artificial Sequence
<220> FEATURE:
<223> OTHER INFORMATION: synthetic sequence

<400> SEQUENCE: 16
gcaactcagg caaagtgaga cat                                         23